(12) United States Patent
Weekly

(10) Patent No.: US 10,785,562 B1
(45) Date of Patent: Sep. 22, 2020

(54) POSITION-AWARE RECORDING DEVICES ABLE TO PROVIDE CONTEXT TO SPEECH

(71) Applicant: Verily Life Sciences LLC, Mountain View, CA (US)

(72) Inventor: David Emmanuel Weekly, Redwood City, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 16/205,143

(22) Filed: Nov. 29, 2018

Related U.S. Application Data

(60) Provisional application No. 62/596,272, filed on Dec. 8, 2017.

(51) Int. Cl.
  *H04R 3/00* (2006.01)
  *G10L 25/84* (2013.01)
  *H04R 1/40* (2006.01)

(52) U.S. Cl.
  CPC .............. *H04R 3/005* (2013.01); *G10L 25/84* (2013.01); *H04R 1/406* (2013.01)

(58) Field of Classification Search
  CPC ......... H04R 3/005; H04R 1/406; G10L 25/84; G10L 15/265; H04W 4/02; G01S 5/0018; G01S 5/0036; G01S 5/18; G01S 5/30; H04L 12/2816; H04L 12/282
  See application file for complete search history.

(56) References Cited

U.S. PATENT DOCUMENTS

| | | | | |
|---|---|---|---|---|
| 10,366,599 B1* | 7/2019 | Hodge | ............... | G08B 21/0211 |
| 2009/0252365 A1* | 10/2009 | Lin | ........................ | H04R 1/08 |
| | | | | 381/369 |
| 2018/0061203 A1* | 3/2018 | Shapiro | .............. | G08B 21/0266 |
| 2018/0096683 A1* | 4/2018 | James | ..................... | H04L 41/12 |
| 2018/0232979 A1* | 8/2018 | Kusens | ............. | G07C 9/00103 |
| 2018/0252793 A1* | 9/2018 | Hazlewood | ............... | G01S 5/18 |

* cited by examiner

*Primary Examiner* — Jason R Kurr
(74) *Attorney, Agent, or Firm* — Perkins Coie LLP

(57) ABSTRACT

Introduced here are recording devices optimized for recording speech between multiple parties (e.g., a speaker and a counterparty, or a first speaker and a second speaker). These recording devices can facilitate the discovery of personalized characteristics of an interaction by detecting location. For example, these recording devices can discover the intent behind certain terms and phrases in the context of a conversation. A recording device can include a communication module configured to stream recorded media content to another electronic device, as well as a marker identification module configured to identify nearby beacons. For example, a recording device may include a Bluetooth® Low Energy chipset configured to identify nearby Bluetooth® beacons and a Wi-Fi® chipset configured to stream recorded media content to another electronic device.

20 Claims, 6 Drawing Sheets

500

501 Acquire audio media related to a conversation

502 Filter non-ultrasonic frequencies from audio media

503 Examine ultrasonic frequencies to identify ultrasonic signature(s)

504 Compare the ultrasonic signature(s) to a mapping table

505 Infer location of speaker(s) based on location of electronic devices corresponding to ultrasonic frequencies

300

301
Identify an audible feature indicative of initiation of a conversation

302
Begin recording audio media

303
Stream the audio media to a network-accessible server system

304
Identify an audible feature indicative of conclusion of the conversation

305
Stop recording audio media

Acquire audio media related to a conversation

402

Acquire location data

403

Parse the audio media and the location data

404

Infer intent behind a specified utterance based on the audio media, location data, or any combination thereof

405

Perform an action based on the inferred intent

501 Acquire audio media related to a conversation

502 Filter non-ultrasonic frequencies from audio media

503 Examine ultrasonic frequencies to identify ultrasonic signature(s)

504 Compare the ultrasonic signature(s) to a mapping table

505 Infer location of speaker(s) based on location of electronic devices corresponding to ultrasonic frequencies

FIGURE 5

POSITION-AWARE RECORDING DEVICES ABLE TO PROVIDE CONTEXT TO SPEECH

CROSS-REFERENCE TO RELATED APPLICATIONS

This application claims priority to U.S. Provisional Application No. 62/596,272, titled "Position-Aware Recording Devices Able to Provide Context to Speech" and filed on Dec. 8, 2017, which is incorporated by reference herein in its entirety.

TECHNICAL FIELD

Various embodiments concern recording devices optimized for recording speech between multiple parties.

BACKGROUND

Medical transcription refers to the process of converting voice-recorded reports, as dictated by healthcare professionals, into text format. Medical transcription has existed since the beginning of the 20th century, when standardization of medical data became critical to research. Medical stenographers initially replaced healthcare professionals as the recorders of medical information. However, with the creation of recording devices, it became possible for healthcare professionals and medical transcriptionists to work asynchronously.

Historically, voice-recorded reports were converted into written documents by medical transcriptionists. A healthcare professional would orally dictate the action(s), effect(s), and/or circumstance(s) accompanying a medical procedure, and then a medical transcriptionist would transcribe the oral dictation. However, these written documents were normally made available only after a significant delay which limited their usefulness, particularly with regard to time-sensitive actions (e.g., rendering diagnoses).

Transcription equipment has changed over the years from manual typewriters to digital recorders. Consequently, speech recognition software has begun replacing medical transcriptionists in the creation of medical transcripts. However, speech recognition software simply cannot capture the nuanced aspects of a conversation that ultimately serve to improve patient outcomes and patient experiences as a whole.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 3 depicts a flow diagram of a process for recording a conversation between multiple parties (e.g., a speaker and a counterparty, or a first speaker and a second speaker).

FIG. 4 depicts a flow diagram of a process for interpreting speaker intent in the context of a conversation.

FIG. 5 depicts a flow diagram of a process for extracting location information from audio media generated by a recording device.

Figure 1:
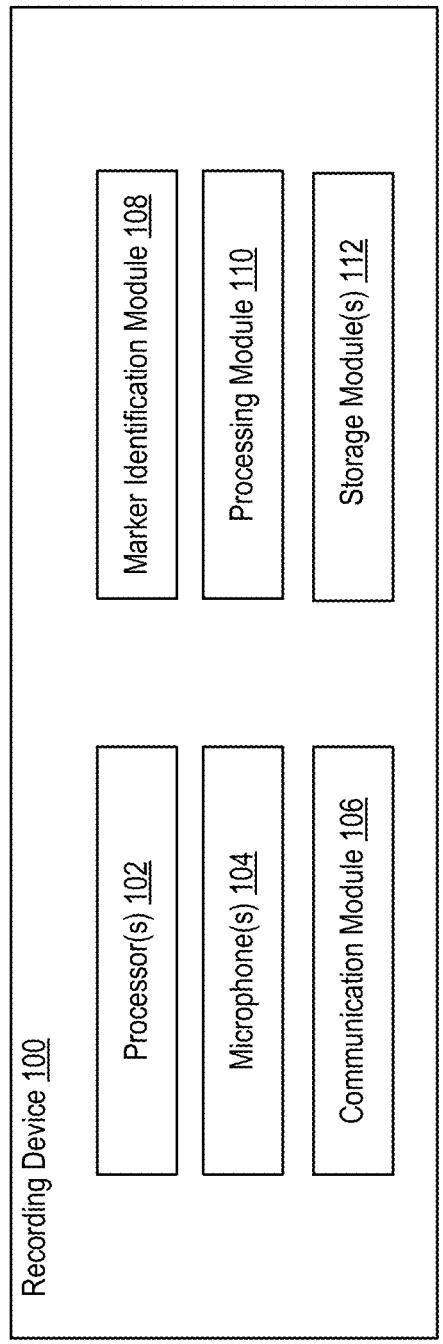
FIG. 1 depicts the high-level architecture of a recording device that facilitates the collection of media content and location data.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Healthcare professionals (also referred to as "medical professionals"), such as physicians, nurses, and researchers, often have face-to-face conversations with patients about complex matters. Entities have begun designing technology in an effort to discover the personalized context of these conversations. For example, some services have begun transcribing conversations recorded by computing devices worn by healthcare professionals. While these services enable information to be associated with patient records, the information is often stored in such a manner that it does not ultimately improve patient outcomes.

These technologies suffer from several other drawbacks as well. For instance, some technologies lead to awkward or uncomfortable interactions. Examples of such technologies include conventional handheld recorders and some wearable electronic devices (e.g., a Google Glass™ wearable computing device). Moreover, some technologies generate an overabundance of information that is not useful in improving patient experiences. For example, a Google Glass™ wearable computing device may visually record an interaction even though the visual output may provide little or no value.

Introduced here, therefore, are recording devices optimized for recording speech between multiple parties (e.g., a speaker and a counterparty, or a first speaker and a second speaker). These recording devices can facilitate the discovery of personalized characteristics of an interaction by detecting the location in which the interaction occurred. By establishing location, a recording device can discover the intent behind certain terms and phrases (also referred to as "utterances") in the context of a conversation. For instance, some phrases (e.g., "patient has experienced an allergic reaction") may take on a different meaning based on whether the phrase was uttered in a hospital waiting room, general examination room, emergency room, etc.

In an example, if a recording device is located in a room with a single patient (which is a normal inpatient setting), the identity of the patient is unambiguous. In such a scenario, the statement "Alert! There has been a heart attack!" communicates implicitly who had the heart attack, and thus can be used to notify nearby attendant(s), the medical professional(s) (e.g., physician) assigned to the patient, etc. In an emergency room setting, however, disambiguation may be needed to determine which patient suffered the heart attack. As further described below, disambiguation can occur in several different ways. For example, when a patient is admitted to a hospital, the patient is normally given a wristband that includes relevant medical information. In some embodiments, an ultrasonic transducer may be included in the wristband to allow for disambiguation (e.g., the patient that a medical professional is presently communicating can be identified based on which ultrasonic transducer (also referred to as an "ultrasonic beacon") is nearest a recording device carried by the medical professional). If medical professionals and patients have such ultrasonic beacons, then it becomes easier to identify which medical professional(s) have communicated with which patient(s). For instance, relevant records can be readily retrieved by uttering, for example, "Which doctor did I talk to before lunch yesterday?"

A recording device can include one or more microphones designed to record a conversation in an optimized manner. As the conversation is recorded, the microphone(s) generate audio media that may be recorded to a memory. The recording device may also include an optical sensor (e.g., a camera, ambient light sensor, or infrared sensor). For example, in some embodiments, the recording device includes a camera configured to generate video media that may be recorded to the memory. Embodiments of the recording device may also include sensor(s) designed for gas detection (e.g., gas leaks, oxygen content, particular contamination, carbon monoxide (CO) levels, carbon dioxide ($CO_2$) levels, wound/necrosis detection), radiation levels, ambient temperature, humidity, heartrate, altitude, etc. Moreover, some embodiments of the recording device are designed such that at least some of the power necessary for operation is generated simply through its motion (e.g., as it swings along a lanyard worn around the neck). The recording device can also include a communication module configured to stream media content (e.g., audio media and/or video media) to another electronic device, as well as a marker identification module configured to identify nearby beacons. For example, a recording device may include a Bluetooth® Low Energy chipset configured to identify nearby Bluetooth® beacons and a Wi-Fi® chipset configured to transmit media content to another electronic device.

Media content recorded by the recording device may be periodically or continually transmitted to another electronic device (e.g., a network-accessible server system) for interpretation, transcription, etc. For example, in some embodiments the recording device streams recorded media content to the network-accessible server system in real time, while in other embodiments the recording device uploads recorded media content to the network-accessible server system on a periodic basis (e.g., hourly, daily, weekly). Additionally or alternatively, the recording device may be able to transmit recorded media content to the network-accessible server system responsive to receiving an instruction to do so. For example, after an interaction with a patient has been completed, a healthcare professional may provide input (e.g., by pressing a button, giving an audible instruction, etc.) indicative of an instruction to upload the corresponding media content to the network-accessible server system.

Because both position and conversational content can be discovered from media content recorded by a recording device, speaker intent can be interpreted in a personalized manner. For example, if a speaker requests that patient-specific information be shown on a display device, then the recording device may be able to select an appropriate display device from multiple nearby display devices. In some embodiments, each display device is named to allow disambiguation. For example, a medical professional may be able to state, "Show x-rays on display one, and show chart on display two." In other embodiments, the recording device can identify an appropriate display device based on the position and/or orientation of the speaker. Thus, simple utterances may provide sufficient context for presenting the correct information on the correct display device.

The recording device may also be configured to identify one or more location markers arranged throughout the ambient environment. Examples of location markers include ultrasonic beacons, Bluetooth® beacons, Wi-Fi® beacons, etc. Location markers can be affixed to doorframes, electronic devices (e.g., display devices, such as computer monitors and televisions), hospital equipment, etc. The recording device can infer additional context based on which location markers, if any, can be detected at a given point in time. For example, if the recording device detects a strong signal that is known to be emitted by a location marker located near a television, then the recording device may determine that information should be shown on the television when a request is uttered by a speaker.

Such technology has several benefits over conventional solutions. For example, the recording device may enable medical professionals to access and navigate wide ranges of information in a seamless, hands-free manner. As another example, conversations can be transcribed and/or associated with medical records in a minimally-invasive manner. Consequently, medical professionals may be able to identify relevant information more quickly, participate in more meaningful interactions with patients, etc.

Embodiments may be described with reference to particular electronic devices, network configurations, networks, etc. However, those skilled in the art will recognize that the features are equally applicable to other electronic devices, network configurations, networks, etc. Moreover, some tasks may be described as being performed by a recording device, while other tasks may be described as being performed by a network-accessible server system. Those skilled in the art will recognize that, in many instances, either the recording device or the network-accessible server system could perform a specified task.

Embodiments may also be described with reference to a particular setting. For example, several embodiments are described in the context of a medical setting in which a medical professional has deployed a recording device. Those skilled in the art will recognize that these examples are provided for the purpose of illustration only. The technology can also be used in other environments in which additional conversational context is useful, such as academic settings, law enforcement settings, etc.

The technology can be embodied using special-purpose hardware (e.g., circuitry), programmable circuitry appropriately programmed with software and/or firmware, or a combination of special-purpose hardware and programmable circuitry. Accordingly, embodiments may include a machine-readable storage medium having instructions that may be used to program an electronic device (e.g., a recording device) to perform a process for generating recordings of conversations, detecting nearby location markers, determining intent behind a particular utterance, taking an action based on the intent, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 depicts the high-level architecture of a recording device 100 that facilitates the collection of media content and location data. As further described below, the recording device 100 may not examine location data to better understand the context of media content. Instead, the recording device 100 may generate media content and location data, and then transmit the media content and the location data to another electronic device for further review.

The recording device 100 can include one or more processors 102, one or more microphones 104, a communication module 106, a marker identification module 108, a processing module 110, and one or more storage modules 112. In some embodiments a single storage module includes multiple computer programs for performing different operations (e.g., speech recognition, noise reduction, filtering), while in other embodiments each computer program is hosted within a separate storage module.

The processor(s) 102 can execute modules from instructions stored in the storage module(s) 112, which can be any device or mechanism capable of storing information. For example, the processor(s) 102 may execute the processing module 110 to parse audio media generated by the microphone(s) 104, prepare a transcript based on the audio media, identify keyword(s) included in the transcript, etc.

The microphone(s) 104 can be configured to record speech uttered by participants in a conversation. In some embodiments, the microphone(s) 104 are omnidirectional microphones designed to pick up sound from all directions. In other embodiments, the microphone(s) 104 are directional microphones (also referred to as "unidirectional microphones") designed to pick up sounds coming from a specific direction. For example, if the recording device 100 is designed to be worn on a lanyard, then the recording device 100 may include at least one microphone arranged to pick up sounds produced by the wearer of the lanyard and at least one microphone arranged to pick up sounds produced by another speaker. In such embodiments, the recording device 100 may include at least one microphone oriented upward (e.g., away from the ground toward the mouth of the wearer) and at least one microphone oriented outward (e.g., away from the body of the wearer). Such an arrangement of microphones ensures that phrases uttered by the wearer and other individual(s) during a conversation can be captured with high fidelity. For example, the processing module 110 may filter audio data generated by a directional microphone based on audio data generated by an omnidirectional microphone (e.g., to reduce the effect of ambient noise). A set of microphones could also be equally spaced to form a phased array able to capture highly-directional audio to reduce captured noise and interference.

In some embodiments, the recording device 100 may be configured to not record speech inputs from anyone other than a user (e.g., the wearer of a pendant that includes the recording device 100). For example, the recording device 100 may include a single directional microphone arranged to record sounds uttered by the user. As another example, the recording device 100 may apply speech processing algorithm(s) to remove sounds uttered by other individuals from audio media recorded by the microphone(s) 104. This may be done for privacy purposes.

The communication module 106 can manage communications between various components of the recording device 100. The communication module 106 can also manage communications between the recording device 100 and another electronic device. For example, the communication module 106 may facilitate communication with a mobile phone, wireless access point (WAP), network-accessible server system, etc. As further described with respect to FIG. 2, the communication module 106 may be configured to transmit data generated by the recording device 100 to a network-accessible server system that includes one or more computer servers for further review. Additionally or alternatively, the communication module 106 can be configured to transmit data generated by the recording device 100 to another electronic device. The other electronic device may be associated with a medical professional (e.g., a physician, nurse, or researcher), medical enterprise/location (e.g., a hospital, nursing home, dentist office), etc. For example, the communication module 106 may transmit data to a mobile phone responsible for processing the data and/or forwarding the data to the network-accessible server system.

The marker identification module 108 can be configured to identify one or more location markers arranged throughout the ambient environment. For example, location markers can be affixed to doorframes, other electronic devices (e.g., display devices, such as computer monitors and televisions), hospital equipment, etc. These location markers enable the recording device 100 (or the network-accessible server system) to infer additional context based on which location marker(s) can be detected before, during, or after a conversation between a medical professional and a patient.

More specifically, the marker identification module 108 can generate location data based on which location markers, if any, can be detected. Generally, a location marker will broadcast a signal that can be detected by the marker identification module 108. For example, ultrasonic beacons may emit a ultrasonic signature (e.g., an inaudible sound with encoded data that uniquely identifies the source), while Bluetooth® beacons and Wi-Fi® beacons may broadcast a unique identifier via Bluetooth® and Wi-Fi®, respectively. Some location markers may be more desirable than others in certain circumstances. For example, ultrasonic signatures can be broadcast by many conventional devices. Bluetooth® beacons, however, may need to be separately installed, powered, etc. Moreover, the marker identification module 108 may be able to determine a proximity to a location marker based on, for example, the strength of the corresponding signal. By estimating the proximity to each detected location marker, the marker identification module 108 can more accurately establish the position of the recording device 100.

Additionally or alternatively, the recording device 100 may emit an ultrasonic signature that uniquely identifies the user (e.g., the wearer of a pendant including the recording device 100). In such embodiments, other electronic devices arranged throughout the ambient environment may be configured to record the ultrasonic signature. For example, network-connected display devices (e.g., televisions and computer monitors) may identify the ultrasonic signature(s) emitted by recording device(s). These other electronic devices may be configured to transmit a signal to the network-accessible server system, either directly or indirectly, responsive to receiving the ultrasonic signature emitted by the recording device 100. In such embodiments, the network-accessible server system can recreate the path traversed by the user based on the signals received from the other electronic devices positioned throughout an environment. In some embodiments, the electronic device that receives the ultrasonic signature may be configured to disambiguate the intent behind an utterance. For example, if a medical professional says, "Display the x-rays on the screen," whichever display device is nearest to the medical professional is likely the intended target of the instruction. Similarly, different beacons could be assigned to different parties. For example, each individual located in a hospital (e.g., patients, visitors, janitors, and medical professionals such as physicians, nurses, etc.) may be associated with a corresponding beacon that implies identity, thereby making the beacon an authentication token of sorts.

Accordingly, the marker identification module 108 may be a Bluetooth® Low Energy chipset, a Wi-Fi® chipset, etc. In some embodiments, the marker identification module 108 and the communication module 106 share a similar architecture. For example, a Bluetooth® Low Energy chipset may be configured to identify nearby location markers and stream media content to another electronic device via a network.

The processing module 110 can apply one or more operations to media content generated by the recording device 100. Examples of media content include audio media generated by the microphone(s) 104, video media generated by a camera, text media generated using an input mechanism (e.g., a keyboard or a stylus), location data generated by the marker identification module 108, etc. Generally, the recording device 100 will produce a stream of media content that includes both conversation regions and pause regions. The processing module 110 can parse the stream of media content to identify distinct conversations. For example, the processing module 110 could determine that the media content should be segmented upon discovering a pause region accompanied by a change in physical context (e.g., based on movement data generated by an inertial measurement unit (IMU) that includes an accelerometer, gyroscope, etc.). Together, the pause region and the change in physical context may be representative of transition to a new conversation. Thus, in some embodiments, the recording device 100 may notify a medical professional (e.g., via an audible alert, tactile alter, or visual alert) that recording will automatically cease following a specified amount of silence (e.g., 30 seconds). If the medical professional does not interact with the recording device 100 within a predetermined amount of time (e.g., 15 seconds) and no further speech is detected, then the recording device 100 may automatically stop recording. In some embodiments, the recording device 100 will create a separate media file for each conversation. For example, the recording device 100 may be configured to begin recording upon recognizing a keyword (e.g., "hello," "initiate recording," or "I'll be recording this conversation") or detecting recognizable sounds.

The recording device 100 may be configured to continually or periodically transmit data to another electronic device. In some embodiments, the recording device 100 streams data to the other electronic device in real time. In such embodiments, the recording device 100 may transmit data to the other electronic device so long as the recording device 100 remains communicatively coupled to the other electronic device. As noted above, the other electronic device may be a mobile phone, tablet computer, mobile computer cart (also referred to as a "hospital computer cart," "medical computer cart," or "mobile workstation"), wireless access point (WAP), network-accessible server system, etc. Thus, the recording device 100 may automatically upload data in response to determining that a conversation between a first participant (e.g., a medical professional) and a second participant (e.g., a patient) has finished. In most instances, each participant could be referred to as a "speaker." However, in some instances, the conversation may be one sided (e.g., there may be a speaker, such as a patient, and a listener, such as a medical professional).

In other embodiments, the recording device 100 uploads data to the other electronic device on a periodic basis. The recording device 100 may upload data hourly, daily, weekly, etc. Data transmitted by the recording device 100 may include multiple subsets of data corresponding to different conversations over a specified time period. For example, a single data file may include seven different audio recordings corresponding to conversations with seven different patients. Additionally or alternatively, the recording device may be able to transmit recorded media content to the network-accessible server system responsive to receiving an instruction to do so. For example, after an interaction with a patient has been completed, a healthcare professional may provide input (e.g., by pressing a button, giving an audible instruction, etc.) indicative of an instruction to upload the corresponding media content to the network-accessible server system. In some embodiments, the recording device 100 is configured (e.g., by the Information Technology (IT) department of a hospital) with a public key for encryption purposes. In such embodiments, whenever data is transferred over a network (e.g., to the network-accessible server system), the recording device 100 can encrypt the data with the public key such that only entities (e.g., the IT department) having the corresponding private key would be able to decrypt the data.

As noted above, the processing module 110 can process data generated by the recording device 100. For example, if the microphone(s) 104 generate audio media, then the processing module 110 may apply noise reduction algorithms or filtering algorithms to improve the signal-to-noise (SNR) ratio. The processing module 110 may also apply speech recognition algorithms to create a transcript of words spoken within the audio media. Note that, in some embodiments, these tasks are instead performed by another electronic device (e.g., a mobile phone or computer server). Given that human speech will generally be the focus of the recording device 100, audio processing algorithms that increase comprehensibility may be desirable, especially if the audio processing algorithms ensure that machine-transcription services can more accurately recognize speech. For instance, most of the useful data in human speech is in the 85-3500 hertz (Hz) range, so the recording device 100 (or the network-accessible server system) may increase the acoustic energy in this band and decrease the acoustic energy in other band(s). Such a technique is often referred to as "audio compression."

Those skilled in the art will recognize that the tasks performed by the components of the recording device 100 could be distributed between the recording device 100 and other electronic device(s) in various manners. For example, the recording device 100 may be responsible for pre-processing audio media recorded by the microphone(s) 104, while a computer server may be responsible for examining the processed audio media to determine the context of specific utterances. As another example, the recording device 100 may be responsible for anonymizing audio media recorded by the microphone(s) 104 (e.g., by removing or altering age- and gender-specific audible features) and associating the anonymized audio media with an identifier (e.g., corresponding to the patient, medical professional, location, setting, etc.), while the computer server may be responsible for examining the anonymized audio media to determine the context of specific utterances. Similarly, the recording device 100 could generate a transcript of audio media recorded by the microphone(s) to shield the identifies of at least some of the speakers and then transmit the transcript to the computer server for further analysis. Thus, some data (e.g., audio media and location data) may reside on the recording device 100, while other data (e.g., processing operations, speech recognition algorithms, maps of location markers) may reside on the computer server.

Embodiments of the recording device 100 may include some or all of the components shown in FIG. 1, as well as other components not shown here.

For example, some embodiments of the recording device 100 include a durable housing (also referred to as a "structural body") that includes one or more openings through which microphone(s) can collect acoustic waves. A first microphone (e.g., a directional microphone) may be arranged adjacent to a first opening in the structural body, and a second microphone (e.g., an omnidirectional microphone) may be arranged adjacent to a second opening in the structural body. In such embodiments, the processing module 110 may filter the first audio data based on the second audio data (or vice versa). For instance, by examining the second audio data, the processing module 110 may discover/filter audible feature(s) that correspond to ambient noise.

For example, some embodiments of the recording device 100 are designed to be hung on a lanyard around the neck of an individual (e.g., a medical professional). In such embodiments, the recording device 100 can include a power component (e.g., a rechargeable battery) and a durable housing that is substantially waterproof.

As another example, some embodiments of the recording device 100 are instantiated as headsets (e.g., in-ear headsets or over-ear headsets). In some embodiments these headsets are single-ear headsets similar to conventional Bluetooth® headsets, while in other embodiments these headsets are over-the-head headsets.

As another example, some embodiments of the recording device 100 are instantiated as accessories for conventional electronic devices and equipment used within medical environments. These embodiments of the recording device 100 may include a durable housing that can be worn (e.g., clipped to belts, smocks/scrubs, laboratory coats, etc.) or carried (e.g., slipped in a pocket). In such embodiments, the recording device 100 can be configured to establish a short-range communication link with another nearby electronic device. For instance, the recording device 100 may be configured to discover nearby location markers via a Bluetooth® communication channel, and then transmit audio media to a computer server over a Wi-Fi® communication channel or a cellular network.

As another example, the tasks described above may be performed by a computer program executing on an electronic device associated with a speaker. Examples of computer programs include web browsers, desktop applications, mobile applications, and over-the-top (OTT) applications. Thus, a speaker (e.g., a medical professional) may download a mobile application onto his/her mobile phone that can initiate recording of audio media, process the audio media, stream the audio media to a computer server, etc. Accordingly, the "recording device" may be a mobile phone if the features described above are embodied in a mobile application.

Figure 2:
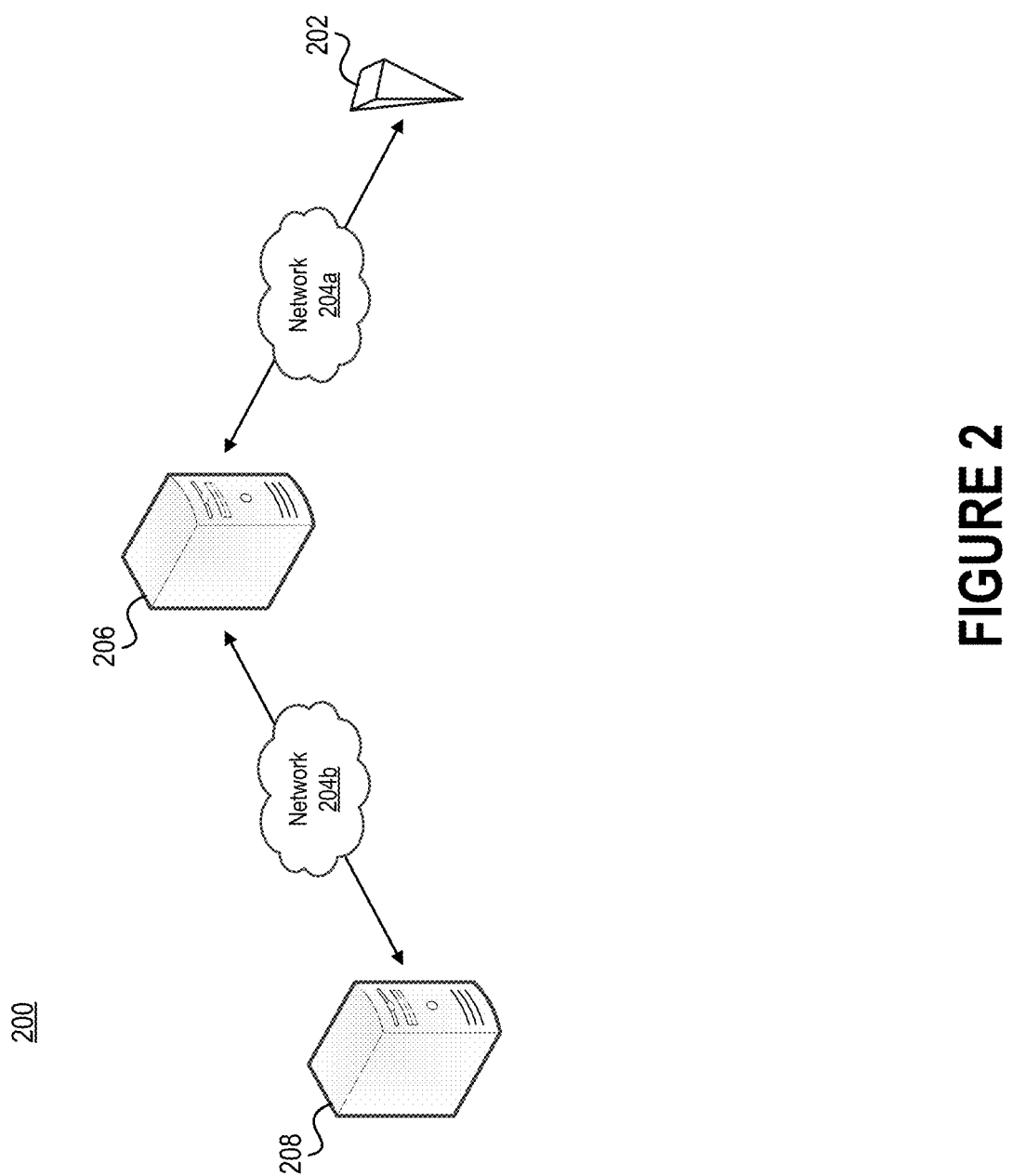
FIG. 2 illustrates a network environment that includes a recording device optimized for recording speech by one or more parties.

FIG. 2 illustrates a network environment 200 that includes a recording device 202 optimized for recording speech by one or more parties (not shown). Intent can be discovered within a conversational context by examining audio media recorded by the recording device 202 in the context of location data generated by the recording device 202.

As noted above, the location data typically specifies which location marker(s) arranged throughout the ambient environment were nearby during a recorded conversation. Thus, the location data may include electronic signatures (e.g., ultrasonic frequencies or Bluetooth® identifiers) that uniquely identify each location marker. Additionally or alternatively, the location data may include supplementary location information, such as WAP identifiers or signal strength, cellular tower identifiers or signal strength, etc.

Those skilled in the art will recognize that the audio media and the location data need not necessarily be separate files. For example, if the recording device 202 is configured to detect unique ultrasonic signatures emitted by location markers, then the location data may be embedded within the audio media. The recording device 202 (or some other electronic device) may need to parse the audio media to discover these ultrasonic signatures, which can be used to infer location throughout the conversation.

The recording device 202 can transmit data to one or more destinations. Here, for example, the recording device 202 transmits data to a network-accessible server system 206. The network-accessible server system 206 can also acquire data from a content server 208. The content server 208 may include, for example, medical records corresponding to the patients with whom a medical professional interacts. The network-accessible server system 206 can supplement the medical records based on information inferred from the data uploaded by the recording device 202. For example, the network-accessible server system 206 may populate database entries based on oral responses recorded by the recording device 202 rather than forms that have been manually filled out by patients.

The recording device 202, network-accessible server system 206, and content server 208 (collectively referred to as the "networked devices") can be connected to one another via computer networks 204a-b. The computer networks 204a-b can include personal area networks (PANs), local area networks (LANs), wide area networks (WANs), metropolitan area networks (MANs), cellular networks, the Internet, etc. Additionally or alternatively, the networked devices may communicate with one another over a short-range communication protocol, such as Bluetooth® or Near Field Communication (NFC). In some embodiments, the recording device 202 communicates directly with the network-accessible server system 206, as shown in FIG. 2. In other embodiments, the recording device 202 communications indirectly with the network-accessible server system 206 (e.g., via one or more other electronic devices). For example, the recording device 202 may be communicatively coupled to a mobile phone via a Bluetooth® communication channel, and the mobile phone may be responsible for transmitting data generated by the recording device 202 to the network-accessible server system 206.

Embodiments of the network environment 200 may include some or all of the networked devices, as well as other devices not shown here. For example, some embodiments of the network environment 200 include a network-accessible server system 206 that only receives data from the recording device 202.

Some of the networked devices may also continue to operate when in an offline mode (i.e., when not connected to any networks). For example, the recording device 202 may record audio media regardless of whether the recording device 202 is connected to a computer network. The recording device 202 may also record timing information generated by a clock module, location information generated by a marker identification module, etc. Such data can be stored in a memory until network connectivity has been re-established.

Some embodiments of the recording device 202 stream wideband audio media inclusive of ultrasonic frequencies to the network-accessible server system 206. The network-accessible server system 206 could then infer speaker location based on the ultrasonic signature(s) discovered in the audio media.

The recording device 202 and/or the network-accessible server system 206 may use knowledge about characteristic(s) of the user of the recording device 202 and/or the ambient surroundings as inputs to improve certain processes, such as speech processing, utterance disambiguating, etc. Examples of characteristics include accents, user history, vocabulary commonly used in a specified setting (e.g., a hospital), vocabulary commonly used by certain individuals (e.g., a particular patient), vocabulary used when discussing certain individuals with certain health conditions, etc. In such embodiments, the recording device 202 and/or the network-accessible server system 206 can employ a feedback loop that provides a transcribed output of audio media produced by the recording device 202 to a professional transcriptionist.

Accordingly, in some embodiments, the recording device 202 and/or the network-accessible server system 206 are configured to learn the accents of different individuals whose speech has been recorded. To accomplish this, a recognition model may be tuned to the formants and/or prosody of a given individual to increase its accuracy in predicting when speech involved the given individual. An onboarding process that requires an individual (e.g., a user of the recording device 202) to repeat certain predefined phrases is generally considered an acceptable way to tune a recognition model for that individual. This approach also has a secondary benefit of offering an additional factor of authentication to partially safeguard against the theft and unauthorized use of the recording device 202 (e.g., to gain access to sensitive information). Thus, the recording device 202 may take certain action (e.g., refuse to record or initiate playback of media content) responsive to discovering that a command was not given by the true owner. Moreover, medical professionals often use different vocabulary (e.g., the conditions seen/discussed by an oncologist may differ than those conditions seen/discussed by a podiatrist or an ophthalmologist). By monitoring the vocabulary of an individual, the recording device 202 and/or the network-accessible server system 206 can disambiguate complex utterances that include rare words (e.g., those related to a certain specialty practice).

Another use case of the recording device 202 is to perform first-pass transcription of audio media to improve human transcription speed. Thus, the recording device 202 can facilitate the editing and creating of transcripts by humans, rather than replace humans entirely. Such a technique enables certain types of editing (e.g., of medical transcripts/records) to be performed much more rapidly.

FIG. 3 depicts a flow diagram of a process 300 for recording a conversation between multiple parties (e.g., a speaker and a counterparty, or a first speaker and a second speaker). A recording device (e.g., recording device 100 of FIG. 1) affixed to, or held by, one of the parties may be responsible for generating audio media related to the conversation.

Initially, the recording device may monitor audible sounds to identify an audible feature indicative of initiation of a conversation (step 301). For example, the recording device may be configured to recognize certain keywords (e.g., "hello," "initiate recording," or "I'll be recording this conversation.") or combinations of certain keywords (e.g., "permission" within a predefined proximity of "granted" or "received"). As another example, the recording device may be configured to recognize values for loudness/intensity, tone, pitch, etc., that signal the conversation has begun. The recording device can then begin recording audio media (step 302).

In some embodiments, the recording device streams the audio media to a network-accessible server system over a computer network (step 303). The recording device may upload the audio media directly to the network-accessible server system or via one or more other electronic devices. For example, the recording device may upload the audio media to a mobile phone via a Bluetooth® communication link, and then the mobile phone may upload the audio media to the network-accessible server system via a Wi-Fi® communication link or cellular communication link.

Additionally or alternatively, the recording device may store at least some of the audio media in a memory. For example, the recording device may be configured to store all audio media in a local memory residing within the recording device. As another example, the recording device may be configured to store audio media in one or more files representative of different segments of the conversation. For instance, each question posed by a first speaker and corresponding answer provided by a second speaker may be stored as a separate file. In such embodiments, these separate files can be readily associated (e.g., by the network-accessible server system) with the appropriate database entries, transcript portions, etc.

The recording device may also monitor audible sounds to identify an audible feature indicative of conclusion of the conversation (step 304). For example, the recording device may be configured to recognize certain keywords (e.g., "thank you," "cease recording," or "goodbye") or combinations of certain keywords (e.g., "thanks" within a predefined proximity of "exit"). As another example, the recognized device may be configured to recognize values for loudness/ intensity, tone, pitch, etc., that signal the conversation has ended. The recording device can then stop recording audio media (step 305).

FIG. 4 depicts a flow diagram of a process 400 for interpreting speaker intent in the context of a conversation. Initially, a network-accessible server system can acquire audio media related to a conversation (step 401). The network-accessible server system may receive audio media recorded by a recording device (e.g., recording device 100 of FIG. 1). However, the audio media may be guided from the recording device to the network-accessible server system by one or more intermediary devices (e.g., mobile phones and WAPs).

The network-accessible server system can also acquire location data pertaining to the speaker(s) involved in the conversation (step 402). In some embodiments, the location data is separately generated by the recording device. For example, the recording device may transmit separate files including audio media and location data, which could include, for example, Bluetooth® beacon signatures or Wi-Fi® beacon signatures. In other embodiments, the location data is derived from the audio media. For example, the network-accessible server system may extract ultrasonic signatures embedded within the audio media.

The network-accessible server system can then parse the audio media and the location data (step 403). Generally, the network-accessible server system performs a series of operations to identify the speaker(s) involved in the conversation, create a transcript of words uttered by the speaker(s), temporally align the audio media and the location data, etc. As further described below with respect to FIG. 5, if the network-accessible server system determines that ultrasonic signature(s) are embedded within the audio media, the network-accessible server system may identify the ultrasonic signature(s), compare the identified ultrasonic signature(s) to a database of sources (e.g., beacons), identify one or more matching sources, establish a location of the recording device throughout the conversation based on the matching source(s), etc.

The network-accessible server system can also infer intent behind a specified utterance based on the audio media, the location data, or any combination thereof (step 404). Properly determining intent will often rely on accurately identifying the location of the speaker and the actual words uttered by the speaker. Said another way, location and content can together provide sufficient context for interpreting the intent behind specific utterances. For example, if a speaker asks for patient-specific information to be shown on a display device, an appropriate display device can be automatically identified after determining the location of the speaker. As another example, if a speaker utters a specific term, appropriate action(s) can be identified after determining the location of the speaker. For instance, different records in a patient profile may be altered if the term "allergy" is uttered in an emergency room rather than a general examination room. The term "location" can be used to refer to position (e.g., within a specified building) or orientation (e.g., which direction a speaker is facing).

The network-accessible server system may perform an action based on the inferred intent (step 405). For example, the network-accessible server system may populate or update a record in a patient profile in response to discovering an instruction to do so within the audio media. The network-accessible server system could also prompt another electronic device to perform an action based on the inferred intent. For example, patient-specific information may be shown on a display device in response to discovering an instruction to perform such action and identifying an appropriate display device. As another example, a prescription may be automatically generated in response to discovering an instruction to perform such action.

Over time, the network-accessible server system may generate a set of learnable skills that can be modified based on the context of a given recording device. Examples of such skills include the ability to add a note to a medical record, request a change to a prescription, book a procedure for a patient, refer a patient to another medical professional (e.g., a specialist), schedule another appointment, alter a treatment plan (e.g., by altering the proposed time of treatment/discharge), summon additional help (e.g., by requesting a specialist, janitor, nurse, etc.), request the patient be moved to another location (e.g., a different room), share information with a designated individual (e.g., a family member of the patient), request a device log a measurement, change the position of a piece of equipment (e.g., a bed), create a note to be sent to the patient for their records, etc. In general, as the number of network-connected devices accessible to a patient increases, the number of voice-addressable interactions also increases.

FIG. 5 depicts a flow diagram of a process 500 for extracting location information from audio media generated by a recording device. Initially, a network-accessible server system can acquire audio media related to a conversation (step 501). Step 501 of FIG. 5 may be substantially similar to step 401 of FIG. 4.

The network-accessible server system can filter non-ultrasonic frequencies from the audio media (step 502). More specifically, the network-accessible server system can apply one or more filters to the audio media to identify ultrasonic frequencies embedded within the audio media. Generally, the filter(s) remove sounds in the audible range (e.g., 20 to 20,000 hertz). Thus, the network-accessible server system may multiplex data channels associated with different frequency bands (e.g., by having different classes of electronic devices transmit data at different ultrasonic frequencies with the intent of having a single multiplexed recording that includes both acoustic speech data and ultrasonic data). When examining the multiplexed recording, the network-accessible server system may truncate the speech data at, for example, 12 kilohertz (kHz), and then shift high-ultrasonic signals (e.g., those between 20-28 kHz) to another frequency range (e.g., 12-20 kHz). Such action would enable recording/playback of these high-ultrasonic signals with a medium that is only capable of handling audible frequencies, such as compact discs (CDs) which can only record up to approximately 22 kHz. Additionally or alternatively, when the audio is played, tones over a certain frequency (e.g., 12 kHz) could simply be filtered out.

The network-accessible server system can then examine the ultrasonic frequencies embedded within the audio media to identify one or more ultrasonic signatures (step 503). The ultrasonic signature(s) may be emitted by ultrasonic beacon(s), conventional electronic devices (e.g., mobile phones, televisions, and computer monitors), or any combination thereof. The network-accessible server system may also compare the ultrasonic signature(s) to a mapping table to identify the source(s) responsible for the ultrasonic signature(s) (step 504). The mapping table, which is hosted in a memory accessible to the network-accessible server system, may include ultrasonic signatures for multiple sources arranged throughout a specified environment, such as a hospital, dental office, operating room, etc.

After identifying the source(s) responsible for the ultrasonic signature(s), the network-accessible server system can infer the location of each speaker involved in the conversation (step 505). More specifically, the network-accessible server system can infer the location of the speaker(s) based on the position of the electronic device(s) responsible for generating the ultrasonic signature(s). The network-accessible server system may infer these locations based on which ultrasonic signature(s) are detected, the strength of each ultrasonic signature, etc. For instance, upon determining that three separate ultrasonic signatures have been detected in audio media, the network-accessible server system may estimate the location of the recording device based on the signal strength of each ultrasonic signature. The network-accessible server system may triangulate the position of the recording device based on the known locations of the three sources and the relative strength of the corresponding ultrasonic signatures.

Those skilled in the art will recognize that some steps in process 300 of FIG. 3, process 400 of FIG. 4, and process 500 of FIG. 5 may be performed locally on the recording device rather than by the network-accessible server system. However, recording devices are often designed to perform minimal processing for several reasons. For example, a recording device may be designed to stream captured audio media to the network-accessible server system to eliminate the need for costly processing components (e.g., processors, larger memory for additional instruction sets, larger power component for additional power consumption). As another example, time-sensitive processes (e.g., examining audio media to detect emergency situations, rendering diagnoses) are normally better suited for other electronic devices, such as mobile phones and mobile computer carts, that have displays, input mechanisms, etc. However, embodiments of the recording device may be designed to perform some steps in these processes.

Unless contrary to physical possibility, it is envisioned that the steps described above may be performed in various sequences and combinations. For example, the process 500 of FIG. 5 may be performed in real time to establish the current location of the recording device. Such action may be useful for knowing where a user (e.g., a medical professional) is located during an emergency situation. Other steps may also be included in some embodiments. For example, the recording device or the network-accessible server system may be configured to dynamically generate a transcript as audio media is received from the recording device. In such embodiments, an individual (e.g., a professional transcriptionist) may review the transcript to ensure consistency, uniformity, etc., and the transcript may be ready for review by the user shortly after a conversation has ended.

Processing System

Figure 6:
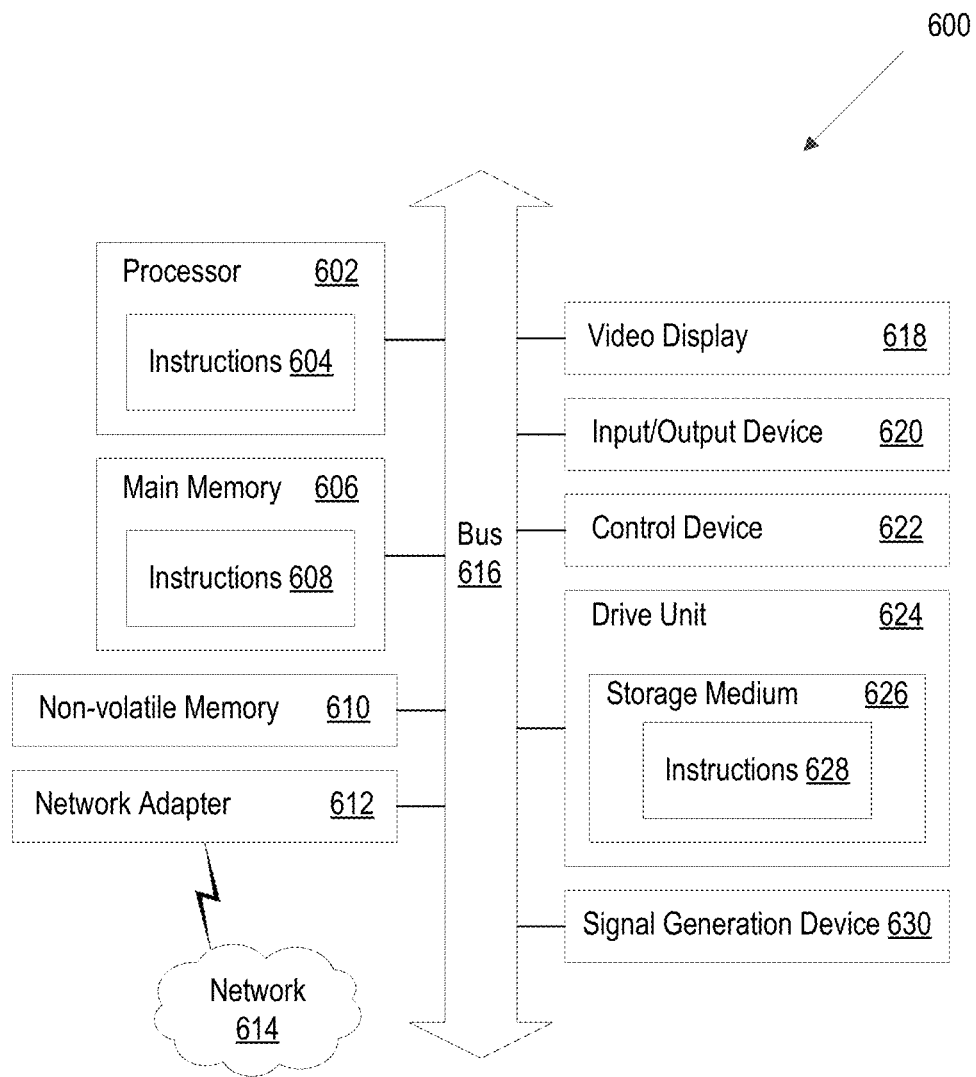
FIG. 6 is a block diagram illustrating an example of a processing system in which at least some operations described herein can be implemented.

FIG. 6 is a block diagram illustrating an example of a processing system 600 in which at least some operations described herein can be implemented. For example, some components of the processing system 600 may be hosted on a recording device able to record conversations between multiple parties. As another example, some components of the processing system 600 may be hosted on an electronic device connected to a recording device across a network.

The processing system 600 may include one or more central processing units ("processors") 602, main memory 606, non-volatile memory 610, network adapter 612 (e.g., network interface), video display 618, input/output devices 620, control device 622 (e.g., keyboard and pointing devices), drive unit 624 including a storage medium 626, and signal generation device 630 that are communicatively connected to a bus 616. The bus 616 is illustrated as an abstraction that represents one or more physical buses and/or point-to-point connections that are connected by appropriate bridges, adapters, or controllers. The bus 616, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 600 may share a similar computer processor architecture as that of a desktop computer, tablet computer, personal digital assistant (PDA), mobile phone, game console, music player, wearable electronic device (e.g., a watch or a fitness tracker), network-connected ("smart") device (e.g., a television or a home assistant device), virtual/augmented reality systems (e.g., a head-mounted display), or another electronic device capable of executing a set of instructions (sequential or otherwise) that specify action(s) to be taken by the processing system 600.

While the main memory 606, non-volatile memory 610, and storage medium 626 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 628. The term "machine-readable medium" and "storage medium" shall also be taken to include any medium that is capable of storing, encoding, or carrying a set of instructions for execution by the processing system 600.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 604, 608, 628) set at various times in various memory and storage devices in a computing device. When read and executed by the one or more processors 602, the instruction(s) cause the processing system 600 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 610, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 612 enables the processing system 600 to mediate data in a network 614 with an entity that is external to the processing system 600 through any communication protocol supported by the processing system 600 and the external entity. The network adapter 612 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 612 may include a firewall that governs and/or manages permission to access/proxy data in a computer network. The firewall may also track varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A recording device comprising:
a structural body that includes multiple openings through which acoustic waves corresponding to sounds external to the structural body can travel;
a directional microphone configured to produce first audio data indicative of the sounds external to the structural body,
   wherein the directional microphone resides within the structural body adjacent to a first opening of the multiple openings;
an omnidirectional microphone configured to produce second audio data indicative of the sounds external to the structural body,
   wherein the omnidirectional microphone resides within the structural body adjacent to a second opening of the multiple openings;
a processing module configured to:
   parse the second audio data to discover an environmental noise,
   alter the first audio data to mitigate an effect of the environmental noise, and
   examine the altered first audio data to identify a conversation involving at least two participants;
an identification module configured to:
   monitor for ultrasonic signals that are broadcast by location markers,
      wherein each ultrasonic signal includes encoded data that identifies the corresponding location marker responsible for broadcasting the ultrasonic signal, and
   generate location data based on a strength of each ultrasonic signal that is presently detectable; and
a communication module configured to:
   initiate a communication channel with a server system across a network, and
   transmit the altered first audio data and the location data to the server system via the communication channel.

2. A recording device comprising:
a microphone configured to produce audio data indicative of sounds produced by a speaker;
a processing module configured to parse the audio data to identify a conversation involving the speaker and at least one other participant;
an identification module configured to
   monitor for signals broadcast by electronic devices located within a specified proximity,
      wherein each signal is broadcast by a corresponding electronic device, and
      wherein each signal includes data that identifies the corresponding electronic device,
   determine that at least one signal is presently being received, and
   generate location data based on a strength of the at least one signal; and
a communication module configured to transmit at least some of the audio data, at least some of the location data, or any combination thereof to a destination across a network.

3. The recording device of claim 2, wherein the microphone is a directional microphone having increased sensitivity to the sounds produced by the speaker.

4. The recording device of claim 2, wherein the microphone is an omnidirectional microphone designed to record sound with substantially equal gain from all directions.

5. The recording device of claim 2, wherein the microphone is one of multiple microphones, and wherein the multiple microphones include:
   a directional microphone having increased sensitivity to the sounds produced by the speaker, and
   an omnidirectional microphone designed to record sound with substantially equal gain from all directions.

6. The recording device of claim 2, wherein the communication module is further configured to broadcast a reference signal that identifies the recording device.

7. The recording device of claim 2, wherein each signal of the at least one signal is an ultrasonic signature of a specified frequency.

8. The recording device of claim 2, wherein the conversation is one of multiple conversations included in the audio data, and wherein the processing module is further configured to:
   create a separate file for each conversation of the multiple conversations by splitting the audio data,
      wherein each separate file includes a subset of the audio data that is related to the corresponding conversation; and
   cause the separate files to be stored in a memory.

9. The recording device of claim 8, wherein the memory resides on a server system, and wherein said causing comprises:
   forwarding the separate files to the communication module for transmission to the server system across the network.

10. The recording device of claim 2, wherein the processing module is further configured to:
   anonymize the audio data by removing or altering an age-specific audible feature, a gender-specific audible feature, or any combination thereof.

11. A method comprising:
   acquiring audio data generated by a microphone of a recording device over the course of a conversation involving a speaker;
   acquiring location data generated by an identification module of the recording device based on a strength of signals that are detected over the course of the conversation,
      wherein each signal is broadcast by a corresponding beacon whose signal can only be detected when located within a specified proximity of the recording device;
   temporally aligning the audio data and the location data to establish a location of the speaker over the course of the conversation;
   deriving an intent behind an utterance in the conversation by analyzing a segment of audio data that includes the utterance and a segment of location data that temporally corresponds to the segment of audio data; and
   performing a specified action based on the intent.

12. The computer-implemented method of claim 11, wherein the identification module is a Bluetooth Low Energy chipset configured to identify whether a beacon is located within a specified proximity based on whether an identifier broadcast by the beacon is presently being received by the Bluetooth Low Energy chipset.

13. The computer-implemented method of claim 11, wherein the identification module is a Wi-Fi chipset configured to identify whether a beacon is located within a specified proximity based on whether an identifier broadcast by the beacon is presently being received by the Wi-Fi chipset.

14. The computer-implemented method of claim 11, further comprising:
   applying a speech recognition algorithm to the audio data to create a transcript corresponding to the conversation.

15. The computer-implemented method of claim 11, wherein said deriving comprises:
   identifying a word included in the segment of audio data;
   establishing a location of the speaker when the word was spoken by examining the segment of location data; and
   predicting the intent based on the word and the location.

16. The computer-implemented method of claim 11, wherein said performing comprises:
   populating a record in a user profile associated with the speaker or another participant in the conversation.

17. The computer-implemented method of claim 11, wherein said performing comprises:
   transmitting an instruction to a display device,
      wherein receipt of the instruction prompts the display device to present information related to the speaker or another participant in the conversation.

18. A method comprising:
   acquiring, by a processor, audio data generated by a microphone of a recording device over the course of a conversation involving a speaker;
   filtering, by the processor, non-ultrasonic frequencies from the audio data;
   examining, by the processor, ultrasonic frequencies remaining in the audio data to identify an ultrasonic signature,
      wherein the ultrasonic signature is an encoded acoustic signal broadcast by a source;
   comparing, by the processor, the ultrasonic signature to a reference database that includes entries for electronic devices arranged throughout an environment,
      wherein each entry associates an electronic device with an ultrasonic signature and a location within the environment;
   determining, by the processor, that the ultrasonic signature matches a record associated with a given electronic device in the reference database;
   establishing, by the processor in response to said determining, that the given electronic device is the source responsible for broadcasting the ultrasonic signature; and
   inferring, by the processor, a location of the speaker involved in the conversation based on a known location of the given electronic device associated with as indicated in the matching record in the reference database.

19. The method of claim 18, wherein the processor resides on the recording device.

20. The method of claim 18, wherein the processor resides on a network-accessible server system that is communicatively coupled to the recording device.

* * * * *